US005138133A

United States Patent [19]

Sakurada et al.

[11] Patent Number: 5,138,133

[45] Date of Patent: Aug. 11, 1992

[54] HEATING SHEET HAVING FAR INFRARED RADIATOR ATTACHED AND VARIOUS EQUIPMENTS UTILIZING HEATING SHEET

[75] Inventors: Kaichiro Sakurada; Takashi Sato, both of Tokyo; Ryoda Sato, 17-6, Kurakuen 3 bancho, Nishinomiya-Shi, Hyogo, all of Japan

[73] Assignees: Think Corporation; Texon Corporation, both of Tokyo; Ryoda Sato, Nishinomiya, all of Japan

[21] Appl. No.: 436,992

[22] Filed: Nov. 15, 1989

[30] Foreign Application Priority Data

Nov. 16, 1988 [JP] Japan ................................ 63-289822

[51] Int. Cl.$^5$ ........................ H05B 11/00; A61N 1/28

[52] U.S. Cl. .................................... 219/211; 219/526; 219/527; 219/528; 219/529

[58] Field of Search ............... 219/211, 212, 526, 527, 219/528, 529; 126/204, 205, 206; 128/399, 64, 24.1; 600/15

[56] References Cited

U.S. PATENT DOCUMENTS

| | | | |
|---|---|---|---|
| Re. 21,474 | 6/1940 | McCleary | 219/46 |
| 1,589,338 | 6/1926 | Wite | 219/211 |
| 3,114,825 | 12/1963 | Kilburn et al. | 219/46 |
| 3,691,349 | 9/1972 | MacColl et al. | 219/549 |
| 3,808,403 | 4/1974 | Kanaya et al. | 219/212 |
| 3,943,912 | 3/1976 | Nakayama | 600/15 |
| 4,533,821 | 8/1985 | Sato | 219/529 |
| 4,540,878 | 9/1985 | Sato | 219/545 |
| 4,736,088 | 4/1988 | Bart | 219/211 |
| 4,825,868 | 5/1989 | Susa et al. | 128/399 |

FOREIGN PATENT DOCUMENTS

| | | |
|---|---|---|
| 62-164509 | 7/1987 | Japan . |
| 62-296850 | 12/1987 | Japan . |
| 0170138 | 3/1989 | Japan . |
| 2132459 | 7/1983 | United Kingdom . |
| 2141010 | 1/1984 | United Kingdom . |

*Primary Examiner*—Bruce A. Reynolds
*Assistant Examiner*—Tuan Vinh To
*Attorney, Agent, or Firm*—Armstrong & Kubovcik

[57] ABSTRACT

A far infrared radiator apparatus which includes a metal wire heating element integrally formed with a radiating device composed of an elastomeric material admixed with a ceramic powder having far infrared radiating properties. The apparatus can be composed of wire fixed to a fabric and coated with the elastomeric material, a heating element coated with far IR radiating elastomeric material to form an integrated body, or wire woven with thread formed of ceramic impregnated material to form a fabric sheet. A radiator apparatus so formed can be made flexible enough to be formed into garments, or various shapes, to heat areas or portions of the body not readily accessible to other heating means.

19 Claims, 8 Drawing Sheets

| Temperature | Amount of Radiant Energy Measured at the Wavelength 7-20μm ($w/m^2$) | Temperature | Amount of Radiant Energy Measured at the Wavelength 7-20μm ($w/m^2$) |
|---|---|---|---|
| 25 | 285 | 70 | 623 |
| 35 | 306 | 75 | 660 |
| 40 | 385 | 80 | 705 |
| 45 | 402 | 85 | 800 |
| 50 | 458 | 90 | 855 |
| 55 | 500 | 95 | 920 |
| 60 | 545 | 100 | 930 |
| 65 | 580 | 105 | 975 |

Measured Conditions

Instrument Used : Far Infrared Radiation Power-meter Manufactured by OPTEX Co. Ltd.

Senser Used : Thermocouple Manufactured by Hitachi Ltd. (CV-Constantan)

HEATING SHEET HAVING FAR INFRARED RADIATOR ATTACHED AND VARIOUS EQUIPMENTS UTILIZING HEATING SHEET

BACKGROUND OF THE INVENTION

This invention relates to a heating sheet to which a far infrared radiator radiating the far infrared rays is attached (in some cases, having magnets attached). It also relates to various equipments which utilizes such heating sheets.

Conventionally, it is known that some type of ceramic radiates the far infrared rays. Also, it is known that the far infrared rays radiated by such ceramic has the action whereby if it is irradiated onto the human body, the circulation of the blood in the irradiated part is improved and consequently one's health is improved.

Such type of ceramic radiates larger amount of the far infrared rays when heated than at a room temperature.

Furthermore, such action is commonly known that if the magnetic force generated by a magnet is applied to the human body, the blood circulation of the part of the body is improved, resulting in contribution to human health.

However, as the above-described type of ceramic is solid, it has been difficult to heat such solid ceramic in a simple manner and to irradiate the far infrared rays generated by the heated ceramic onto the human body effectively.

Furthermore, when a heater consisting of a nichrome wire is used as a heating source for the ceramic, it often happens that the nichrome wire breaks and generates sparks. In other cases, the user can get injured due to the generated sparks or high heat, or even a fire may occur.

SUMMARY OF THE INVENTION

The object of the present invention is to provide a simple-structured heating sheet having a far infrared radiator attached in which the ceramic is heated in a simple manner, the far infrared rays are irradiated onto the human body effectively, and the temperature of the heating source for heating the ceramic is low so as to avoid burning or fire occurence.

Another object of the present invention is to provide various equipments utilizing such heating sheet.

A further object of the present invention is to provide various equipments which can apply magnetic force as well as the far infrared rays onto the human body effectively.

Yet another object of the present invention is to provide a heating sheet having a far infrared radiator attached comprising a heating sheet which is formed by weaving wires made of a metal having low resistivity with nonconductive threads and which is constructed so that the metal wires are connected to a power source, and a far infrared radiator which is made by kneading silicone rubber, silicone varnish vinyl chloride, epoxy resin or urethane resin with a powder of a far infrared rays radiating material to be mixed therewith, and having the far infrared radiator attached at a prescribed position of the heating sheet.

A still further object of the present invention is to provide supporters, a supporter for the hip, a belly belt and a shoulder-covering garment each of which is constructed by changing the shape of the above-described heating sheet having the far infrared radiator attached.

An additional object of the present invention is to provide supporters, a supporter for the hip, a belly belt, and a shoulder-covering garment each of which is constructed by attaching magnets to the above-described respective equipments.

Another object of the present invention is to provide a heating apparatus having a far infrared radiator attached comprising a bag-shaped fabric case having a long transverse side, a heating sheet which is formed by weaving wires which is made of a metal having low resistivity with nonconductive threads and is constructed so that the metal wire is connected to the power source, and a band-shaped far infrared radiator which is made by kneading silicone rubber, silicone varnish, vinyl chloride, epoxy resin or urethane resin to be admixed with a powder of a far infrared rays radiating material; the heating sheet and far infrared radiator being inserted in the case.

Further object of the present invention is to provide an apparatus including a heating sheet having a far infrared radiator attached which is formed by combining a wire made of a metal having low resistivity with a cloth of a prescribed shape, applying silicone rubber, silicone varnish, vinyl chloride, epoxy resin or urethane resin kneaded with the powder of the far infrared rays radiating material thereon, and in which both ends of the metal wire are connected to a power source.

DESCRIPTION OF THE PREFERED EMBODIMENT

Figure 1:
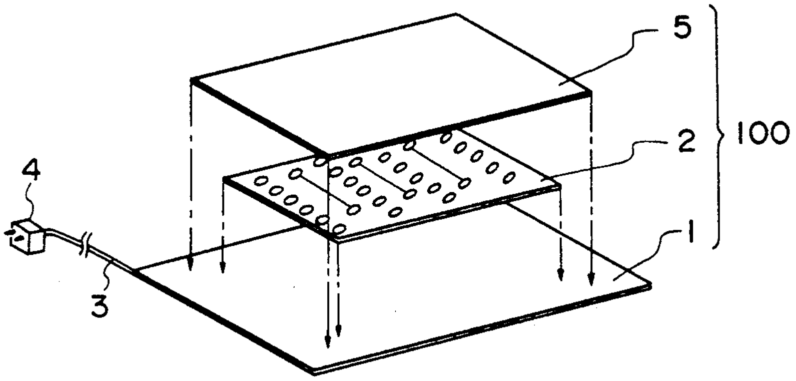
FIG. 1 is an exploded perspective view showing the manufacturing procedures of an apparatus including a heating sheet having a far infrared radiator attached according to the present invention.

FIG. 1 is an exploded perspective view showing the manufacturing procedures of a heating sheet having a far infrared radiator attached according to the present invention. As shown in FIG. 1, the heating sheet having the far infrared radiator attached 100 is constructed by placing a far infrared radiator 2 on a heating sheet 1 and sewing a holding cloth 5 placed on top of the infrared radiator together with the heating sheet to form an integrated apparatus. Reference numeral 3 denotes a lead wire attached to the heating sheet 1 and reference numeral 4 an adapter attached to the end of the lead wire 3.

Each component of the apparatus including heating sheet having the far infrared radiator attached 100 is now to be described in detail.

Figure 2:
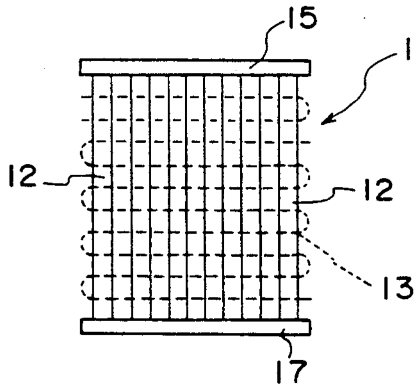
FIG. 2 is a plan view showing the basic structure of a heating sheet.

FIG. 2 shows the basic structure of the heating sheet 1. As illustrated in FIG. 2, the heating sheet 1 is constructed by weaving metal wires 12 made of a metal having low resistivity with nonconductive threads 13 such as synthetic resin thread or cotton thread. An example of the metal having low resistivity is stainless steel.

At both ends of the metal wires 12, two band-shaped feeding sections 15, 17 which are placed in parallel to each other are attached so that the metal wires 12 will form a plurality of parallel circuits. The feeding sections 15, 17 are composed of metal wire and they are also woven with the nonconductive threads 13.

Although it is not illustrated in FIG. 2, two wires within the lead wire 3 shown in FIG. 1 are connected to the feeding sections 15, 17 respectively.

If, for example, voltage of 12 V is applied to the heating sheet 1, it will be warmed up, for example, to 42° C. The actual temperature depends on the length of the metal wires 12, its diameter and other conditions.

Figure 19A:
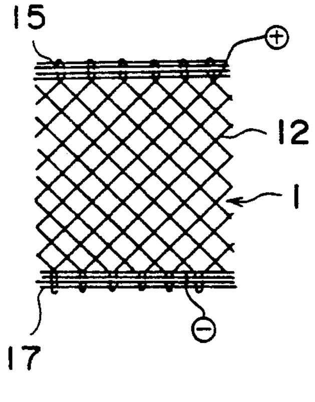
FIG. 19(*a,b*) is a plan view of another type of heating sheet having the far infrared radiator attached according to the present invention.
Figure 19B:
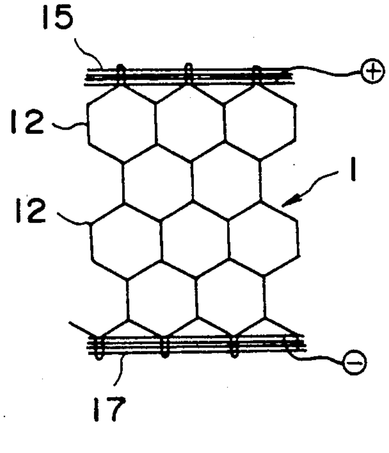

The construction of the metal wires 12 is not restricted to that shown in FIG. 2, namely the metal wires 12 being connected in parallel with reference to the feeding sections 15, 17. For example, the feeding sections 15, 17 may be diagonally mounted to the metal wires 12 which are forming grids, as shown in FIG. 19(A). Furthermore, the metal wires may be arranged in hexagonal mesh as illustrated in FIG. 19(B).

Thus, a variation of the heating sheet 1 is possible. If the heating sheet satisfies the conditions, namely that it is constructed by weaving metal wires having low resistivity with nonconductive thread and that the metal wires are heated when they are connected to a power source, any other structural variation is possible.

The lead wire 3 taken out of the heating sheet 1 is connected to an adapter 4, as illustrated in FIG. 1. The adapter 4 has a function whereby if it is connected to the domestic power source of 100 V, for example, it reduces the voltage to 12 or 24 V. If the structure of the adapter 4 is varied, it is possible to use the car battery as the power source of the heating sheet.

Figure 3:
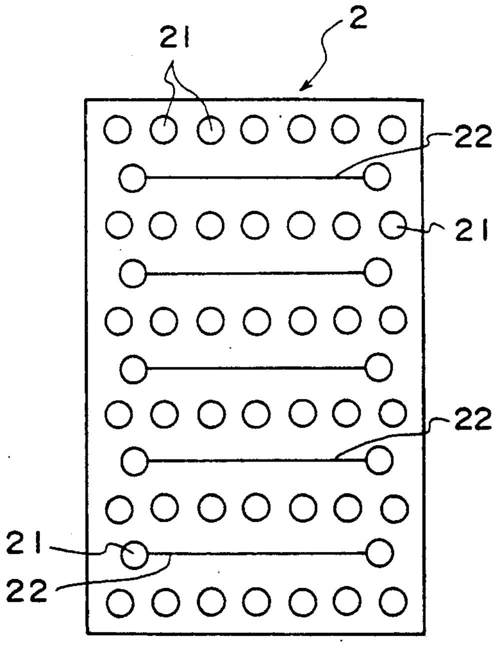
FIG. 3 is a plan view of a far infrared radiator.

FIG. 3 is a plan view showing the far infrared radiator 2. The far infrared radiator 2 is composed of silicone rubber kneaded with a ceramic powder. The far infrared radiator is formed into a thin sheet and it has a plurality of through holes 21. Between a prescribed pair of through holes, a slit 22 is formed which also penetrates the thin sheet.

Since the far infrared radiator 2 is composed of elastic silicone rubber and has the through holes 21 and slits 22 formed, if it is pulled in the longitudinal direction of the diagram, not only the silicone rubber stretches but the slits 22 open such that the radiator 2 stretches more compared with when the through holes and slits are not formed, and thus its elasticity is improved. Furthermore, the presence of the through holes 21 improves the permeability to the air between the top and bottom sides of the far infrared radiator 2. The shapes and positions of the through holes 21 and slits 22 are not restricted to those shown in FIG. 3, but various alternatives are possible.

The ceramic powder used to form the far infrared radiator 2 has an average particle diameter equal to or less than approximately 2.5 μm.

The ceramic used to form the far infrared radiator 2 is a calcined ceramic which radiates the far infrared rays. As to its components, for example, cordierite ($2MgO.2Al_2O_3.5SiO_2$), spinel ($MgO.AL_2O_3$), zircon compound (e.g. a compound mainly composed of $ZrO_2.SiO_2$ and mixed with manganese oxide, MnO), or a mixture of above-mentioned compounds is used.

It is to be understood that the material used as the ceramic is not limited to those mentioned above, but any ceramic can be used if it radiates the far infrared rays. Furthermore, its particle diameter may be varied in accordance with the purpose of its application.

The manufacturing method of the heating sheet having the far infrared radiator attached 100 is now to be described.

Figure 4:
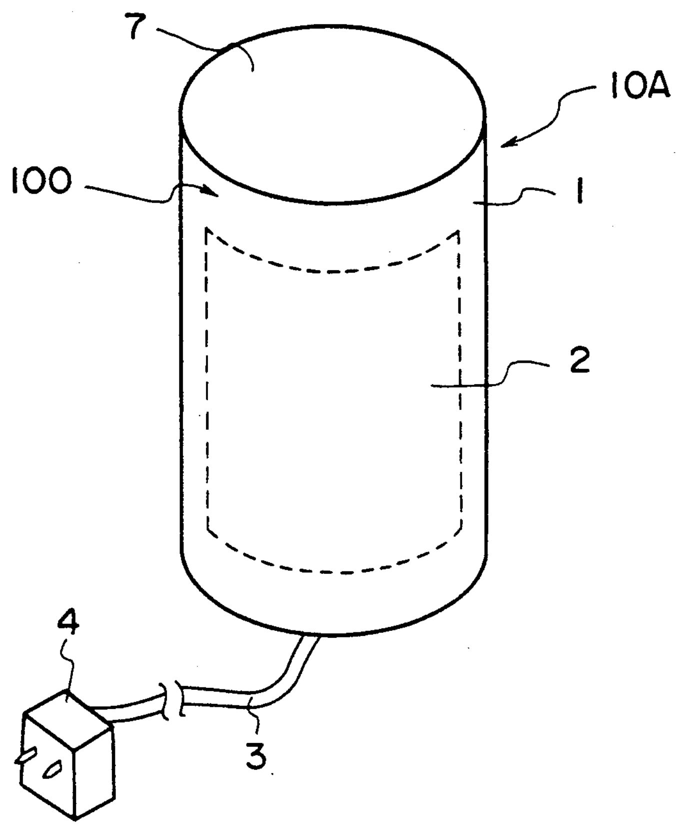
FIG. 4 is a perspective view showing an embodiment of an apparatus the present invention wherein the heating sheet having the far infrared radiator attached is used as a supporter.

FIG. 1 shows the manufacturing method of the heating sheet having the far infrared radiator attached 100 which is illustrated in FIG. 4.

As in FIG. 4, in order to form the heating sheet having the far infrared radiator attached 100, the infrared radiator 2 of FIG. 3 is placed on the prescribed position of the heating sheet 1 of FIG. 2. Then, a holding cloth 5 which is slightly larger than the far infrared radiator 2 is placed on top of the far infrared radiator 2 and the holding cloth 5 is fixed to the heating sheet 1 by sewing around the entire edge of the cloth 5. Thus, the far infrared radiator 2 is fixed to the heating sheet 1 and the heating sheet having the far infrared radiator attached according to the present invention is completed.

FIG. 4 is a perspective view showing an embodiment of the present invention wherein the heating sheet having the far infrared radiator attached 100 is used as a supporter. As shown in FIG. 4, the supporter 10A comprises the heating sheet having the far infrared radiator attached 100 shown in FIG. 1 and a fabric member 7 which is attached in order to shape the heating sheet 1 into a form of a cylinder.

Figure 5:
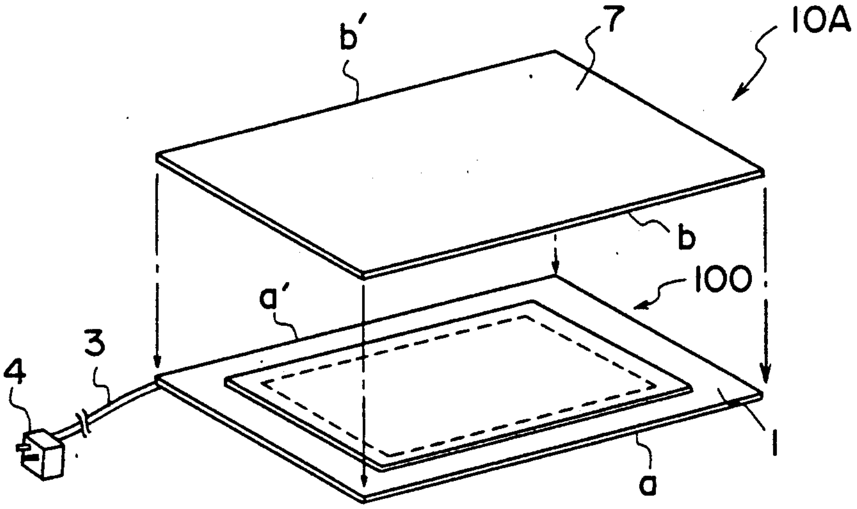
FIG. 5 is an exploded perspective view showing the manufacturing procedures of the supporter illustrated in FIG. 4.

FIG. 5 shows the manufacturing procedures of the supporter 10A of FIG. 4. As illustrated in FIG. 5, a fabric member 7 which is of the same shape as the heating sheet 1 is placed on top of the heating sheet having the far infrared radiator attached 100. The heating sheet having the far infrared radiator attached 100 and the fabric 7 are sewn together along their longer sides aa' and bb', respectively. Thus, the cylinder-shaped supporter 10A as shown in FIG. 4 is obtained.

The supporter 10A is put on the elbow or knee of a user, for example, and the adapter 4 is connected to the power source. Then, the heating sheet is heated to warm up the knee or elbow. At the same time, the far infrared radiator and the ceramic contained therein are heated so as to increase the amount of far infrared rays radiated by the ceramic greatly.

Figures 6, 11:
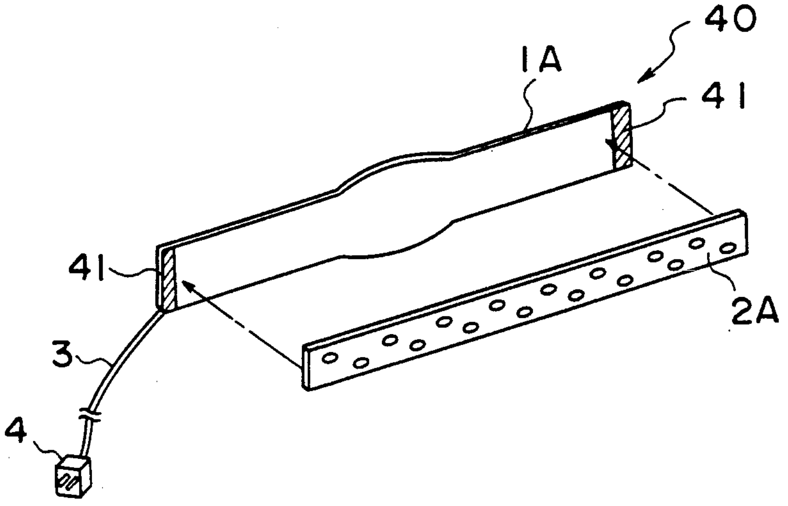
FIG. 6 is a table showing the relationship between the temperature of the ceramic and the far infrared radiant energy radiated by the ceramic.
FIG. 11 is an exploded perspective view showing an embodiment wherein the heating sheet having the far infrared radiator attached according to the present invention is used as a belly belt.

FIG. 6 shows the relationship between the ceramic temperature and the radiant energy of the far infrared rays radiated by the ceramic (measured at the wavelength of 7-20 μm). Here, spinel ($MgO.2Al_2O_3$) is used as the ceramic.

As shown in FIG. 6, the amount of the radiant energy of the ceramic ($W/m^2$) increases with the temperature increase.

Thus, if the supporter 10A is used, a large amount of the far infrared rays is irradiated onto the affected part of the knee or elbow. Consequently, the blood circulation is improved and sweating is stimulated far more than when a supporter made of the heating sheet alone is used. Furthermore, as the current flows through the metal wires 12 of the heating sheet 1, the magnetic field is generated around the wire to produce magnetic effect which further improves the blood circulation of the affected part.

The supporter 10A is manufactured so that the far infrared radiator 2 is placed inside of the heating sheet 1. However, it can be manufactured so that the far infrared radiator 2 is placed outside of the heating sheet.

Figure 7:
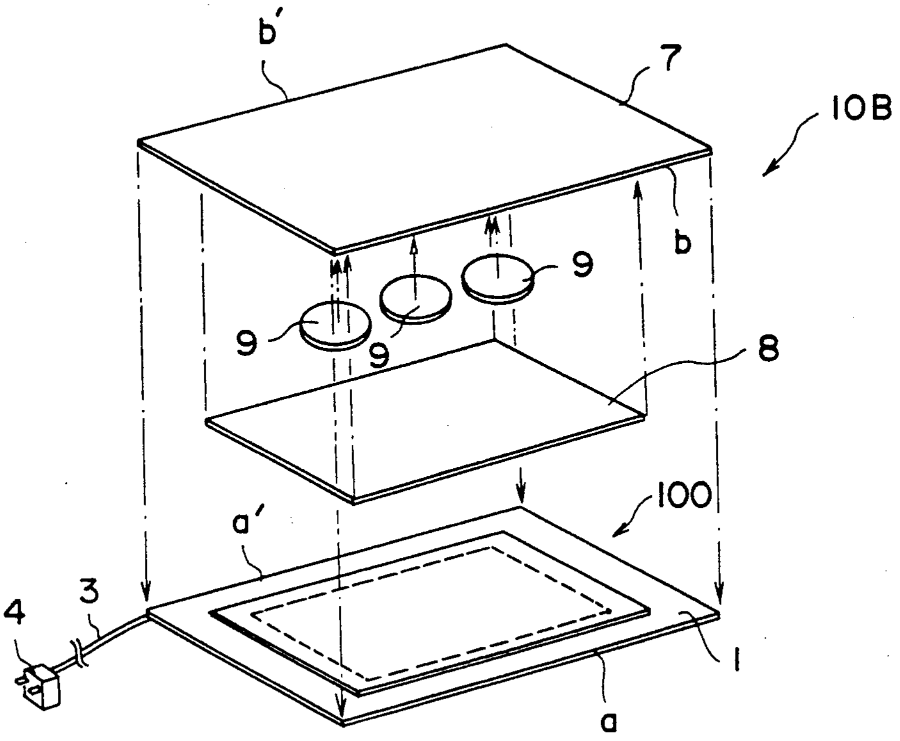
FIG. 7 is an exploded perspective view showing the manufacturing procedures of another type of supporter according to another embodiment of the present invention.

FIG. 7 shows the manufacturing procedures of the supporter 10B according to another embodiment of the present invention utilizing the heating sheet having the far infrared radiator attached 100.

As illustrated in FIG. 7, three disk-shaped magnets 9 are attached on the bottom side of the fabric member 7 in this embodiment. The magnets 9 are fixed on the fabric member 7 by sewing a fabric member 8 which covers the magnets from the bottom side of the fabric member 7 onto the fabric member 7. Then, the fabric member 7 is placed on the heating sheet having the far infrared radiator attached 100. The longer sides aa', bb' of the fabric member 7 and the heating sheet having the far infrared radiator attached 100 are sewn together respectively to form the cylinder-shaped supporter 10B. According to the present embodiment, not only the far infrared rays but also the magnetic force generated by the magnets can be irradiated onto the body. This improves the blood circulation even more effectively.

Figure 8:
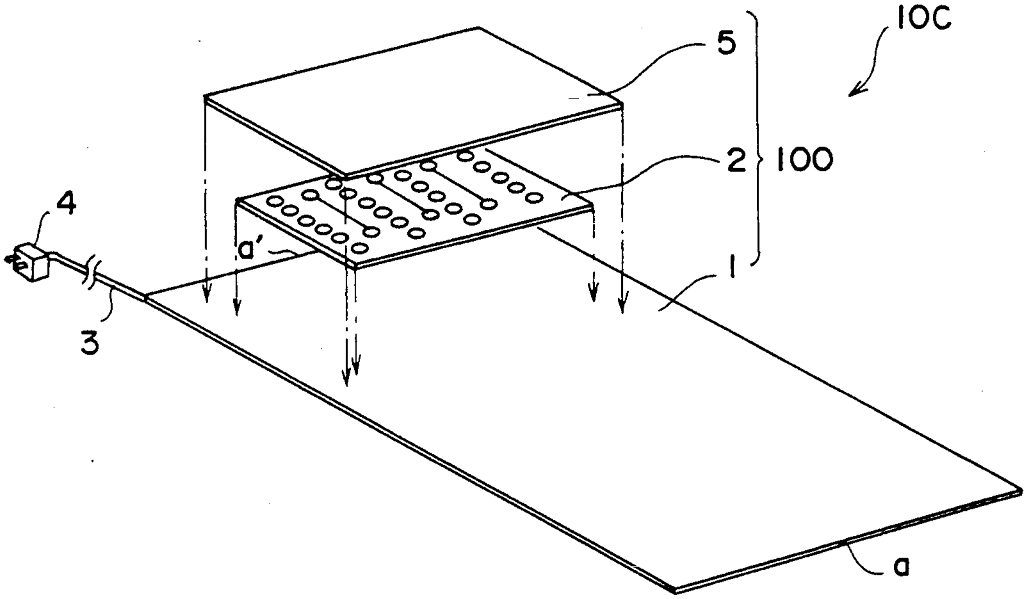
FIG. 8 is an exploded perspective view showing the manufacturing procedures of another type of supporter according to another embodiment of the present invention.

FIG. 8 shows the manufacturing procedures of the supporter 10C according to another embodiment of the present invention.

As illustrated in FIG. 8, differing from the supporter 10A of FIG. 5, the heating sheet 1 is shaped into a rectangle having an elongated transverse side and no fabric member 7 is used. The holding cloth 5 is sewn to a portion of the heating sheet with the far infrared radiator 2 in-between. Then the shorter sides aa' of the heating sheet 1 are sewn together to form a cylindrical supporter 10C.

Thus, the supporter 10C is manufactured without using the fabric member 7.

Figure 9:
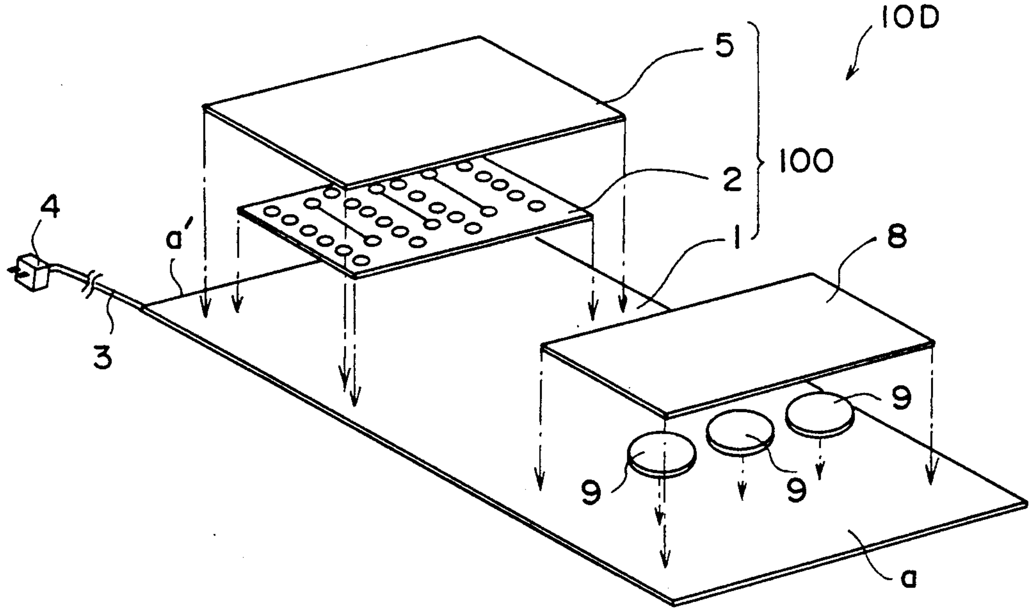
FIG. 9 is an exploded perspective view showing the manufacturing procedures of another type of supporter according to another embodiment of the present invention.

FIG. 9 shows the supporter 10D which is another embodiment of the present invention.

As illustrated in FIG. 9, the supporter of this embodiment is the supporter 10C of FIG. 8 having magnets 9 fixed. Thus, the magnets 9 are arranged on the prescribed part of the heating sheet 1 which is free of the far infrared radiator and they are attached to the heating sheet 1 by sewing the fabric member 8. The sides aa' of the heating sheet 1 are sewn together to form the cylindrical supporter 10D.

Figure 10:
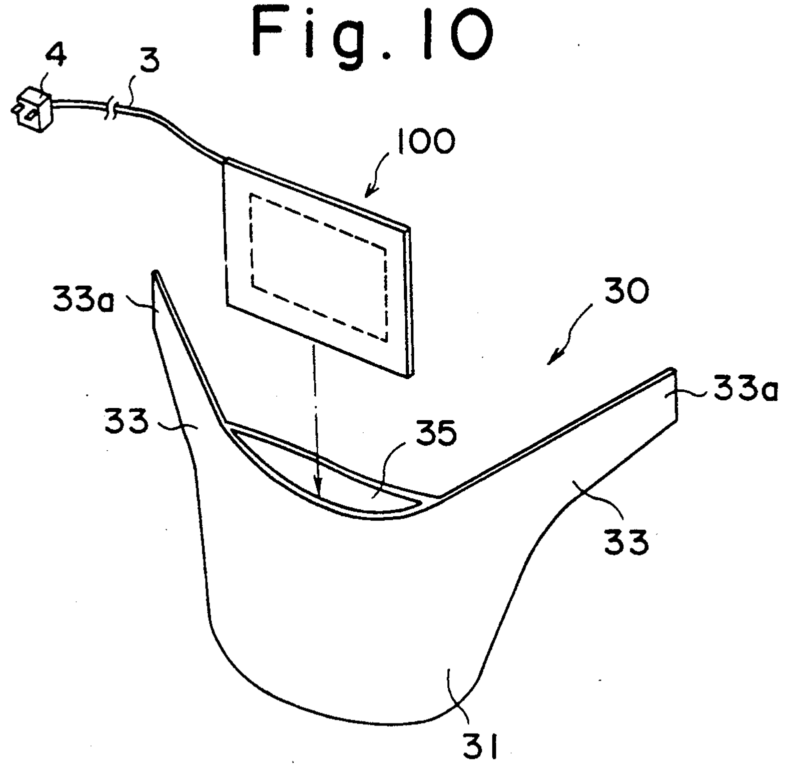
FIG. 10 is an exploded perspective view showing an embodiment wherein the heating sheet having the far infrared radiator attached according to the present invention is used as a supporter for hip.

FIG. 10 shows the embodiment of the present invention wherein the heating sheet having the far infrared radiator attached 100 is used as a supporter for the hip 30.

As illustrated in FIG. 10, the supporter for the hip 30 comprises a hip-covering portion 31 which is made of a material such as fabric and is shaped to a size to cover the hip, a pocket 35 which is provided in the hip-covering portion, a heating sheet having a far infrared radiator attached 100 which has the structure shown in FIG. 4 and is inserted in the pocket 35, and band sections 33, 33 each of which is attached to respective side of the hip covering portion.

In order to use the supporter for hip 30, the hip-covering portion 31 is placed on the user's hip, the band sections 33, 33 are brought to the front of his body to join the end portions 33*a*, 33*a* of the band sections 33, 33 and the adapter 4 is connected to the power source. In this manner, the same effects as those of the supporter 10A mentioned earlier can be applied to the hip.

FIG. 11 is an exploded perspective view showing the embodiment of the present invention wherein the heating sheet having the far infrared radiator attached is used as a belly belt 40.

As in FIG. 11, the belly belt 40 of this embodiment comprises a band-shaped far infrared radiator 2A having the same basic structure as illustrated in FIG. 3 and a band-shaped heating sheet 1A having the same basic structure as in FIG. 2, the far infrared radiator 2A being either adhered or sewn to one side of the heating sheet 1A. Magic tapes 41, 41 which enables flexible attachement and/or detachment of the ends of the heating sheet 1A are fitted thereon.

The heating sheet 1A is wound on the user's belly and the magic tapes 41,41 on the ends thereof are joined together, and the adapter 4 is connected to the power source. Thus, the belly belt 40 is fixed on the belly portion of the user and the same effects as those of the supporter 10A mentioned earlier are obtained.

Figure 12:
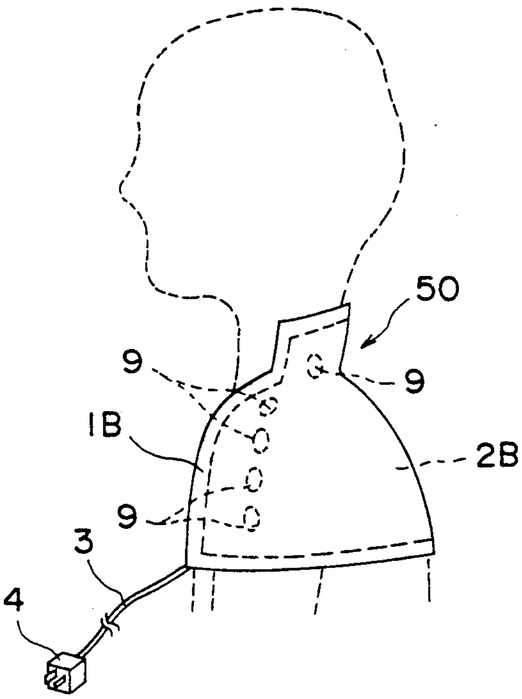
FIG. 12 is an exploded perspective view showing an embodiment according to the present invention wherein the heating sheet having the far infrared radiator attached is used as a shoulder-covering garment.

FIG. 12 shows the embodiment of the present invention wherein the heating sheet having the far infrared radiator attached is used as a shoulder-covering garment 50. As shown in FIG. 12, the shoulder-covering garment 50 of this embodiment comprises a heating sheet 1B which has the same basic structure as the heating sheet 1 of FIG. 2 and is shaped so that it will cover the shoulders and the back of the neck of the user, and a far infrared radiator 2B having the same basic structure as that illustrated in FIG. 3 and having the approximately same shape as the heating sheet 1B, the far infrared radiator 2B being adhered or sewn to the heating sheet 1B.

If the user puts the shoulder-covering garment on his shoulders and the adapter is connected to the power source, the far infrared rays are radiated onto the user's shoulders and neck from the far infrared radiator effectively, and the same effects as the case of the supporter 10A mentioned earlier are obtained.

The magnets 9 can be fixed around the neck or shoulder portions of the shoulder-covering garment 50.

Figure 13:
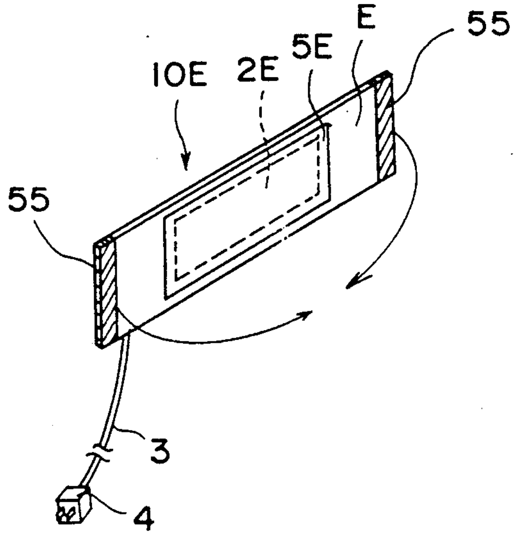
FIG. 13 is an exploded perspective view showing an embodiment according to the present invention wherein the heating sheet having the far infrared radiator attached is used as another type of supporter.

FIG. 13 is an exploded view showing another type of supporter 10E utilizing the heating sheet having the far infrared radiator attached according to the present invention.

As shown in FIG. 13, the supporter 10E comprises a heating sheet 1E which has the same structure as the heating sheet 1 of FIG. 2 and whose transverse sides are elongated, a far infrared radiator 2E placed thereon, a holding cloth 5E which is placed on top of the far infrared radiator 2E and sewn to the heating sheet 1E, and magic tapes 55, 55 which are attached on both ends of the heating sheet 1E and enables flexible attachment and/or detachment thereof.

The supporter 10E is wound around on the desired portion of the user's body such as the arm or leg, and the magic tapes are joined to fix the supporter 10E on the desired position. Then, the adapter 4 is connected to the power source to obtain a large amount of far infrared radiation from the far infrared radiator 2E onto the user's body effectively.

The supporter 10E can be put on various parts of the body flexibly even if their sizes are different.

Figure 14:
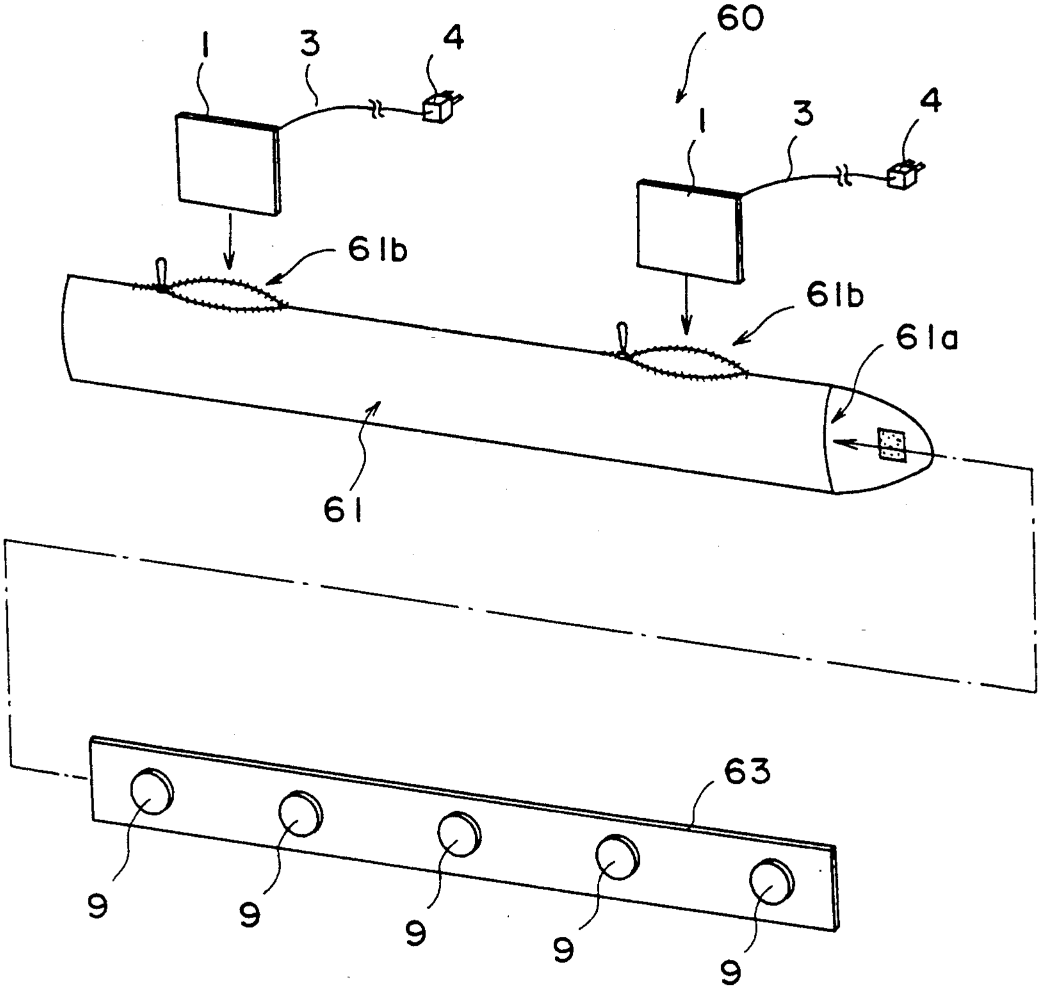
FIG. 14 is an exploded perspective view showing the manufacturing procedures of another type of apparatus including a heating sheet having the far infrared radiator attached according to the present invention.

FIG. 14 shows another type of the heating sheet having the far infrared radiator attached according to the present invention.

The heating sheet having the far infrared radiator attached 60 comprises a case 61 having an elongated transverse side, heating sheets 1 and far infrared radiator 63, both of which are inserted in the case 61. The details of its structure is to be described hereinafter.

Two pieces of fabric shaped to have long opposing transverse sides are sewn together along the upper and lower edges and the left-hand side edge. Thus formed bag-shaped case 61 has an opening 61*a* at the right-hand side. Along the upper side of the case 61, two openings having zippers attached are provided to form pockets 61*b*, 61*b*.

The heating sheets 1 of FIG. 2 having the lead wire 3 and adapter 4 affixed are used.

The material of the far infrared radiator 63 is urethane resin kneaded with the ceramic powder. It is, then, shaped into a band to form the far infrared radiator 63. Five disk-shaped magnets 9 are attached to the far infrared radiator 63.

Figure 15:
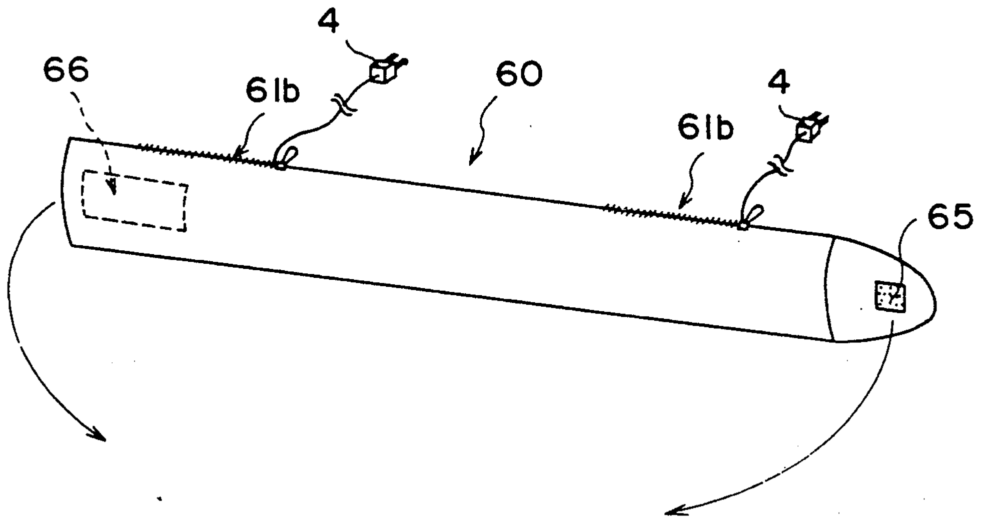
FIG. 15 is an exploded perspective view of the apparatus including a heating sheet having far infrared radiator attached manufactured in accordance with the procedures shown in FIG. 14.

To assemble the heating sheet having the far infrared radiator attached 60, the far infrared radiator 63 is inserted into the case 61 through the opening 61*a* and the heating sheets 1, 1 are placed in the pockets 61*b*, 61*b* respectively, and then the zippers of the pockets 61*b*, 61*b* are closed. FIG. 15 shows the assembled heating sheet having the far infrared radiator attached 60.

The assembled heating sheet having the far infrared radiator attached 60 is wound around the user's belly and the magic tapes 65, 65 which are fitted at both ends of the heating sheet having the far infrared radiator attached 60 are joined on the user's belly. If the adapter 4,4 are connected to the power source, the heating sheet 1 is heated and warms the far infrared radiator 63 resulting in a large amount of the far infrared radiation from the far infrared radiator.

Figure 16A:
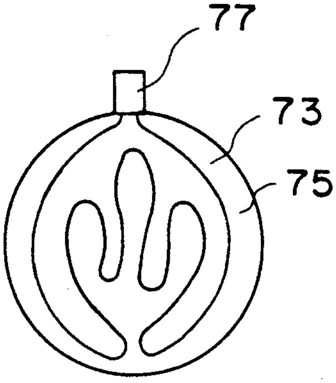
FIG. 16(*a,b*) FIG. 17(*a,b*) and FIG. 18(*a,b*) are views showing the manufacturing procedures of a pendant apparatus utilizing another type of heating sheet having far infrared radiator attached according to the present invention.
Figure 16B:
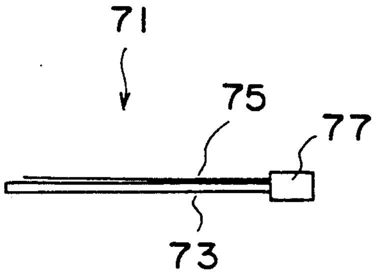
Figure 17A:
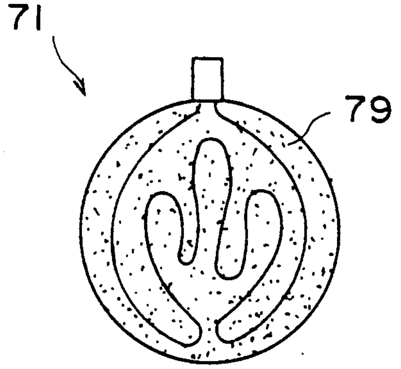
Figure 17B:
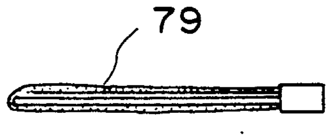
Figure 18A:
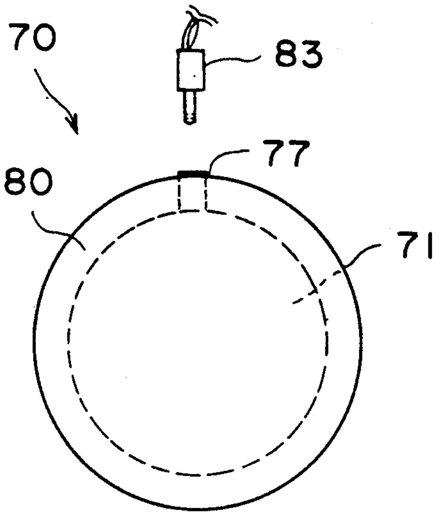
Figure 18B:
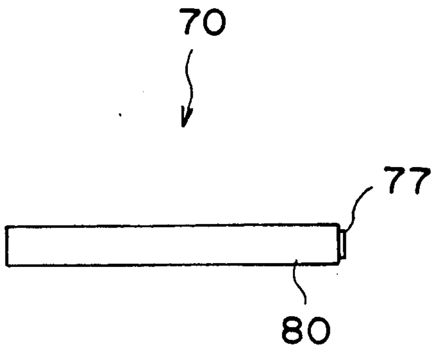

FIGS. 16, 17, 18 show the manufacturing methods of a pendant 70 utilizing the heating sheet having the far infrared radiator attached. FIGS. 16(A), 17(A), 18(A) are plan views, and FIGS. 16(B), 17(B), 18(B), are side views, respectively.

As shown in FIG. 16, the metal wire 75 made of a metal having the low resistivity is placed on a piece of cloth 73. Both ends of the metal wire 75 are connected to a female terminal 77. Then, the cloth 73 arranged with the metal wire 75 is immersed in the silicone rubber melted by heating, then taken out to solidify the silicone rubber deposited on the cloth 73 so that the metal wire and cloth are coated with the silicone rubber. The melted silicone rubber has been kneaded with the same ceramic powder as that used to form the far infrared radiator 2 of FIG. 3. In this manner, manufactured is a heating sheet having the far infrared radiator attached 71 wherein the cloth 73, metal wire 75 and far infrared radiator composed of the silicone rubber kneaded with the ceramic powder are integrated. Then, as shown in FIG. 18, the heating sheet having the far infrared radiator attached 71 is placed in a case 80 made of a synthetic resin to complete the pendant 70.

As illustrated in FIG. 18(A), a male terminal 83 is connected to the female terminal 77 and the other end of the male terminal 83 is connected to the power source (not illustrated in the diagram). Thus, the far infrared radiator 79 within the pendant 70 is heated to radiate the far infrared rays outwards from the pendant 70.

The heating sheet having the far infrared radiator attached 71 can be utilized as a remedy for piles. Though not illustrated, the heating sheet having the far infrared radiator attached 71 of FIG. 17 is attached to the part of the user's underpants or underpants-shaped-supporter which opposes the user's anus. Then, the male terminal 83 shown in FIG. 18 is connected to the female terminal 77 and a current is let flow in the metal wire 75 to radiate the far infrared rays from the far infrared radiator 79 onto the anus. As a result, the blood circulation around the anus is improved.

So far, the heating sheet having the far infrared radiator attached according to the present invention and equipments utilizing it have been described in detail. However, the present invention is not restricted to those specific embodiments, but, 1) The shape or form of the far infrared radiator or heating sheet can be widely varied according to its usage.

2) The usage of the heating sheet having the far infrared radiator attached is not restricted to those above-mentioned embodiments. But, the heating sheet having the far infrared radiator attached according to the present invention can be utilized in any way if it is put on the user's body (for example, a head band).

3) The heating sheet having the far infrared radiator attached 100 shown in FIG. 1 is formed by placing the far infrared radiator on the heating sheet 1 and then covering the far infrared radiator with the holding cloth 5. However, the holding cloth 5 is not always required, but the far infrared radiator 2 can be fixed to the heating sheet 1 directly by sewing or adhering.

4) The basic material of the far infrared radiator 2 is not limited to silicone rubber, but can be other material such as silicone varnish, vinyl chloride, epoxy resin, or urethane resin.

Furthermore, the heating sheet having the far infrared radiator attached according to the present invention can be obtained by the powder of far infrared radiating material with a coating material such as silicone varnish and by applying thus-manufactured coating material on the heating sheet 1.

5) The thread 13 of FIG. 2 may be a thread of synthetic resin such as an acrylic resin which is kneaded to be mixed with the powder of ceramic radiating the far infrared rays. Thus, if such thread is woven with the metal wire 12 to form a fabric of the heating sheet 1, the heating sheet 1 itself radiates the far infrared rays without the far infrared radiator 2 of FIG. 3 attached.

What we claim is:

1. A far infrared radiator apparatus comprising:

metal wire having low resistivity fixed to a fabric of a desired shape;

said fabric with said wire fixed thereto being coated with an elastomer material selected from the group consisting of silicone rubber, silicone varnish, vinyl chloride, epoxy resin and urethane resin, said selected material having admixed therewith a powder of far infrared radiating material; and means for connecting said metal wire to a power source to heat said radiating material.

2. A far infrared radiator apparatus according to claim 1, wherein said far infrared radiator apparatus is formed into a thin sheet having openings comprising at least one of a plurality of through holes and penetrating slits formed therein.

3. A far infrared radiator apparatus according to claim 1, wherein said far infrared radiating material is calcined ceramic powder having an approximate average particle diameter equal to or less than 2.5 μm.

4. A supporter comprising a far infrared radiator apparatus according to claim 1, 2 or 3 on top of a fabric member having the same shape as said far infrared radiator apparatus and formed into a cylinder.

5. A supporter according to claim 4 wherein magnets are fixed at prescribed positions of said fabric member and far infrared radiator apparatus.

6. A supporter comprising a far infrared radiator apparatus according to claim 1, 2 or 3 sewn to form a cylinder.

7. A supporter according to claim 6 wherein magnets are fixed on prescribed positions of said far infrared radiator apparatus.

8. A supporter for the hip comprising a hip-covering portion of a desired shape, a pocket being formed in said hip-covering portion to contain a far infrared radiator apparatus according to claim 1, 2 or 3, and band sections fixed to sides of the hip-covering portions to be wound around a user's waist and joined to fix the hip-covering portion on the hip.

9. A supporter for the hip according to claim 8, wherein magnets are fixed on prescribed positions of said supporter for the hip.

10. A belly belt formed of a far infrared radiator apparatus according to claim 1, 2, or 3, and having magic tapes fixed on end portions to enable flexible attachment and detachment thereof.

11. A shoulder-covering garment comprising a far infrared radiator apparatus according to claim 1, 2, or 3 formed so that it will cover a user's shoulders and back of the neck.

12. A shoulder-covering garment according to claim 11, wherein magnets are fixed on the prescribed positions of said garment.

13. A far infrared radiator apparatus comprising:

an electric heating element formed of metal wire having low resistivity; and a far infrared radiator composed of an elastomer material kneaded to be admixed with a ceramic powder having far infrared radiating properties;

said heating element being coated with said elastomeric material and ceramic powder to form an integrated body; and means for connecting said heating element to a source of electric powder to heat said body.

14. A far infrared radiator apparatus according to claim 13 wherein magnets are fixed on said far infrared radiator apparatus.

15. A pendant comprising said far infrared radiator apparatus according to claim 13 accommodated in a case.

16. An underpants comprising said far infrared radiator apparatus according to claim 13 fixed on a portion of underpants opposing a user's anus.

17. A radiator apparatus as recited in claim 13, wherein said body is formed with openings therein to increase flexibility and stretchability of said body.

18. A heating and radiating apparatus comprising:

metal wire having low resistivity;

thread formed of synthetic resin kneaded to be admixed with a ceramic powder having far infrared radiating properties;

said metal wire being woven with said thread to form a fabric sheet; and means for connecting said metal wire to a source of electric powder to pass electricity therethrough so as to heat said fabric sheet and thereby cause far infrared radiation to be emitted by said ceramic powder.

19. A far infrared radiator apparatus comprising:

metal wire of low resistivity including means for connecting said wire to a source of electric power for heating said wire; and an elastomeric synthetic resin admixed with a ceramic powder having far infrared radiating properties;

said metal wire and elastomeric synthetic resin being formed integrally into a sheet-like material.

* * * * *